(12) United States Patent
Sparks et al.

(10) Patent No.: US 8,016,798 B2
(45) Date of Patent: Sep. 13, 2011

(54) FLUID DELIVERY SYSTEM AND SENSING UNIT THEREFOR

(75) Inventors: Douglas Ray Sparks, Whitmore Lake, MI (US); Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 1999 days.

(21) Appl. No.: 10/708,509

(22) Filed: Mar. 9, 2004

(65) Prior Publication Data

US 2004/0171983 A1 Sep. 2, 2004

Related U.S. Application Data

(63) Continuation-in-part of application No. 10/248,839, filed on Feb. 24, 2003, now Pat. No. 6,932,114.

(60) Provisional application No. 60/530,961, filed on Dec. 10, 2003, provisional application No. 60/469,134, filed on May 12, 2003.

(51) Int. Cl.
*A61M 5/00* (2006.01)

(52) U.S. Cl. .......................................... 604/246; 604/65

(58) Field of Classification Search .................. 604/246, 604/131, 890.1–892.1, 65–67, 533–284
See application file for complete search history.

(56) References Cited

U.S. PATENT DOCUMENTS 4,321,461 A * 3/1982 Walter et al. .................... 377/21
6,477,901 B1 * 11/2002 Tadigadapa et al. ..... 73/861.352

* cited by examiner

*Primary Examiner* — Theodore Stigell
*Assistant Examiner* — Phillip Gray
(74) *Attorney, Agent, or Firm* — Hartman & Hartman, P.C.; Gary M. Hartman; Domenica N. S. Hartman

(57) ABSTRACT

A fluid delivery system capable of delivering a precise amount of fluid, such as a fluid required for medical treatment. The delivery system makes use of an inline sensing unit that includes a housing comprising an inlet for receiving a fluid from a fluid source, an outlet for discharging the fluid from the housing, and at least one cavity between the inlet and the outlet. A sensing element and electronic circuitry are disposed within the at least one cavity. The electronic circuitry is adapted to produce an electrical output based on at least one response of the sensing element. The sensing unit is further equipped with a communication element for providing communication between the electronic circuitry and an electronic device remote from the housing.

4 Claims, 4 Drawing Sheets

FLUID DELIVERY SYSTEM AND SENSING UNIT THEREFOR

CROSS REFERENCE TO RELATED APPLICATIONS

This application a continuation-in-part patent application of co-pending U.S. patent application Ser. No. 10/248,839 filed Feb. 24, 2003 to Sparks, now U.S. Pat. No. 6,932,114 and claims the benefit of U.S. Provisional Application No. 60/530,961, filed Dec. 10, 2003, and U.S. Provisional Application No. 60/469,134, filed May 12, 2003.

BACKGROUND OF INVENTION

1. Field of the Invention

The present invention generally relates to fluid handling devices and methods for their use. More particularly, this invention relates to a fluid delivery system and an inline sensing unit capable of delivering controlled amounts of fluids.

2. Description of the Related Art

Infusion therapy generally involves the administration of a medication to a subject using intravenous (IV), subcutaneous and epidural routes. A wide variety of fluid infusion pumps have been developed over the years that are capable of delivering medication at a controlled rate. Such pumps include elastomeric, gravity fed, syringe, electrical and mechanical pumps. Valves and flow sensors have been incorporated into some infusion pump designs to improve dosage accuracy and to control the flow of fluids (e.g., drugs, medications, etc.) through these systems. More recently, micromachined flow sensors, valves and pumps have been developed, some of which have been used in medication and drug delivery applications. Precise fluid control and measurement made possible with the above equipment and devises can also be useful in other medical applications, such as drug compounding and urological and blood analysis.

Certain types of infusion therapies require extremely small amounts of fluids to be delivered in a very precise manner. In these situations, hand-actuated syringes are often not sufficiently accurate. Furthermore, hand-actuated syringes are prone to many types of human errors such as errors in dosage amount, dose rate, and medicine type. Machine-controlled pumps are capable of significantly better accuracy. For example, the accuracy of infusion pumps typically ranges from about +/−15% for volumetric pumps, down to about +/−3% for syringe pumps. Though Coriolis mass flow sensors can provide flow rate measuring accuracies of under +/−1%, their high cost and general requirements for relatively high flow rates have restricted their use in the medical field.

Commonly-assigned U.S. Pat. No. 6,477,901 to Tadigadapa et al. discloses a sensing device having a micromachined resonating tube that operates on the basis of the Coriolis effect to sense mass flow and density of a flowing fluid. The device can sense extremely low volumetric flow rates (e.g., less than 1 ml/hr) of the type required by drug delivery applications. The device uses an electrostatic drive and capacitive sensing, and therefore requires little power for its operation. Commonly-assigned and copending U.S. patent application Ser. No. 10/248,839 to Sparks utilizes the sensing device disclosed in Tadigadapa et al. in a fluid delivery system capable of delivering a precise amount of fluid and monitoring certain properties of the fluid so that the correct fluid is safely delivered to its intended destination. The fluid delivery system of Sparks is also equipped to measure elapsed time and to stop fluid flow in response to output signals of the sensing device. This micromachined sensor is ideal for obtaining the high accuracy, at low power levels and small size that is needed for drug infusion, compounding and medical analysis systems.

While Tadigadapa et al. and Sparks provide significant advancements for infusion systems and treatments, further improvements would be desirable.

SUMMARY OF INVENTION

The present invention provides a fluid delivery system capable of delivering a precise amount of fluid, such as a fluid required for medical treatment, while also monitoring certain characteristics or properties of the fluid so that the correct fluid is safely delivered in controlled amounts to its intended destination. The system makes use of an inline sensing unit that, in a preferred embodiment, contains a flow sensor of the type disclosed in U.S. Pat. No. 6,477,901 to Tadigadapa et al., wherein a micromachined resonating tube operates on the basis of the Coriolis effect to sense mass flow and/or density of a flowing fluid.

The inline sensing unit of this invention includes a housing comprising an inlet for receiving a fluid from a fluid source, an outlet for discharging the fluid from the housing, and at least one cavity between the inlet and the outlet. A sensing element mounted within the at least one cavity is adapted to have a first response to the density and a second response to the mass flow rate of the fluid flowing between the inlet and the outlet of the housing. Electronic circuitry disposed within the at last one cavity is adapted to produce an electrical output based on at least one of the first and second responses of the sensing element. The inline sensing unit is further equipped with a communication element for providing communication between the electronic circuitry and an electronic device remote from the housing.

A fluid delivery system equipped with the inline sensing unit described above is capable of delivering a precise amount of fluid, in terms of mass flow rate and volumetric flow rate, and can be further used to sense dosage dispensed through the unit. The functionality of the sensing unit can be enhanced to include visual and/or audible signals in response to the density, flow rate, and/or dosage of the fluid. The fluid delivery system can also be equipped to store such data and other information in memory, and/or relay such data and information to a computer Based on the data and information, the flow of the fluid can be stopped if one or more of these parameters are outside preset limits. In this manner, the sensing unit is capable of monitoring blockage. Based on fluid density measurements, the sensing unit is also able to detect gas bubbles or another phase within the fluid, and can determine whether, based on density, the correct fluid is being delivered. This capability can also be employed to prevent medication delivery errors and avoid venous air embolisms.

The inline sensing unit and fluid delivery systems equipped with the sensing unit can be adapted for a variety of applications within and outside the medical industry. If used to intravenously deliver fluids, the sensing unit can be placed inline of a variety of fluid delivery components, including syringes, pipettes, cannula, catheters, Y-ties (Y injection site), septums, machine-controlled pumps, IV primer/drip chambers, etc. In one particular example, the sensing unit is mounted to a manually-operated syringe, with a hypodermic needle mounted to the outlet of the housing. The sensing unit improves the safety and accuracy of manual drug infusion safety performed with syringes by sensing both the mass flow rate and density of the fluid being dispensed, from which the volumetric flow rate and, by the incorporation of a timing device, dosage can be calculated and displayed to the user. Using the preferred sensing element of Tadigadapa et al., the present invention enables manually-operated syringes and pipettes to deliver fluids with nanoliter and microliter control, a capability otherwise impossible with a manually-operated syringe or pipette. As syringes are generally intended to be disposable, the sensing unit of this invention can be manufactured so that the housing comprises a disposable portion in which components that contact the fluid (e.g., the sensing element, inlet, and outlet) are contained, and a separable reusable portion in which components that do not contact the fluid (e.g., the electronic circuitry and communication element) are contained.

Other objects and advantages of this invention will be better appreciated from the following detailed description.

DETAILED DESCRIPTION

Figure 1:
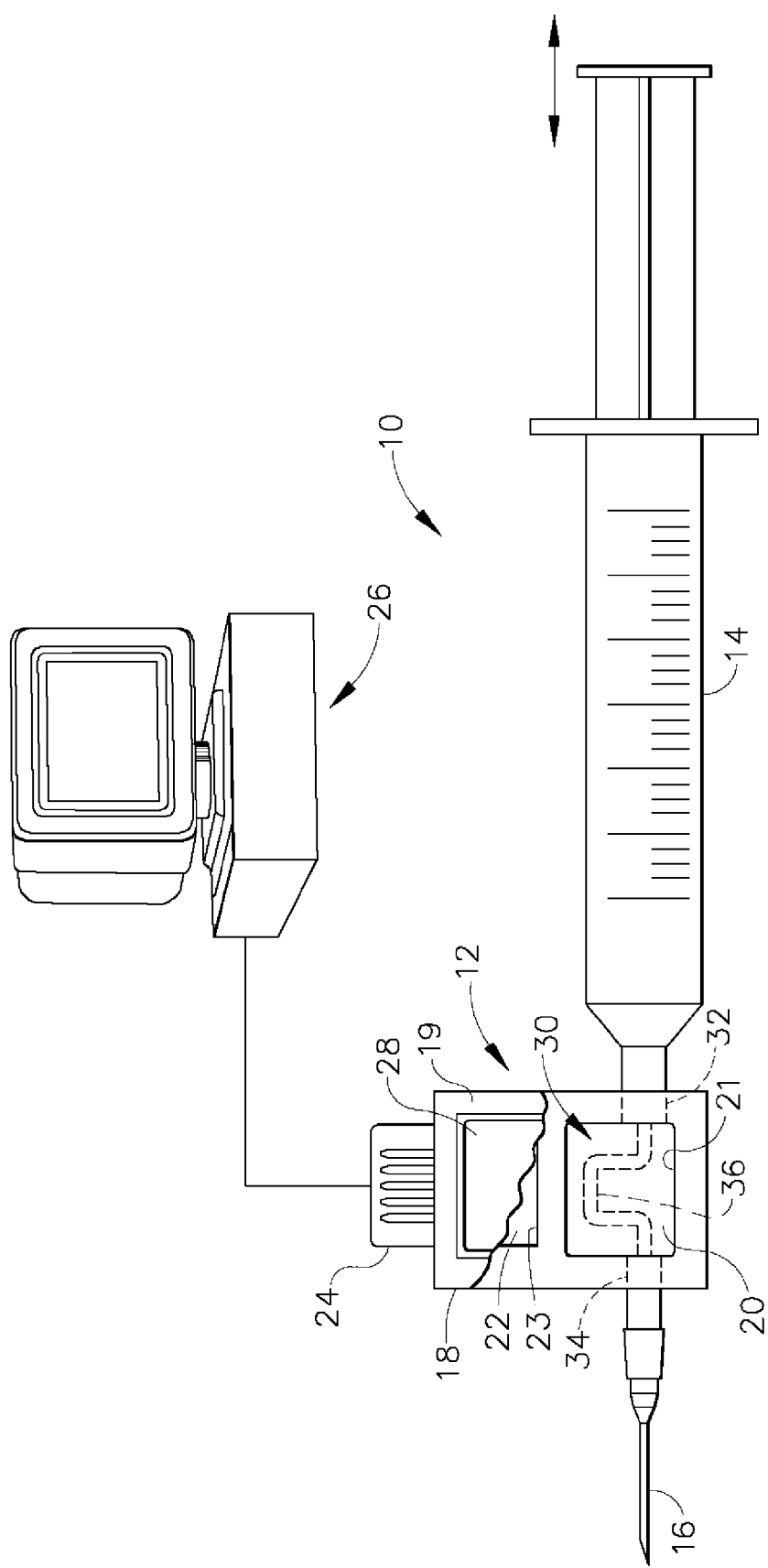
FIG. 1 is a schematic representation of a fluid delivery system adapted for use with a manually-operated syringe in accordance with a first embodiment of this invention.

With reference to FIG. 1, a fluid delivery system 10 is shown that utilizes an inline sensing unit 12 through which a fluid flows for delivery from a manually-operated syringe 14, through a hypodermic needle 16, and to a patient. The sensing unit 12 is termed "inline" because the unit 12 is physically mounted between the fluid source and the device that delivers the fluid to its intended destination. As will become evident from the following, a variety of fluid sources could be used in place of the syringe 14, including Y-ties, septums, machine-controlled pumps, IV primer/drip chambers, etc. Furthermore, a variety of accessories could be used in place of the needle 16, including IV tubes, pipettes, cannula, catheters, etc. As such, the fluid delivery system 10 can be used to administer medications by a variety of methods, e.g., intravenous, intra-arterial, subcutaneous, intramuscular (IM), intraperitoneal (IP), intrathecal, transdermal, etc.

According to a preferred aspect of this invention, the sensing unit 12 comprises a housing 18 in which a sensing element 20 and electronic circuitry 22 are enclosed. As indicated in FIG. 1, the sensing element 20 and circuitry 22 are located within cavities 21 and 23 defined within the housing 18 and closed by a cover 19 (shown in partial section). In the embodiment shown, the housing 18 is an integral portion of the syringe 14, and is therefore simultaneously molded with the barrel portion of the syringe 14. However, the housing 18 could be separately formed and secured to the syringe 14 is so desired. For example, the housing 18 could be coupled to the syringe 14 (or another drug delivery apparatus) through a fluidic connection such as a Luer, threaded, compression, barbed, lock or other type of fitting.

FIG. 1 also shows means for providing communication between the electronic circuitry 22 and an electronic device remote from the housing 18, namely, an electrical connector 24 by which the circuitry 22 can be coupled to a remote computer 26, though a microprocessor or another suitable electronic device capable of controlling the sensing unit 12 could also be used. While the computer 26 is represented as being hard-wired to the sensing unit 12, the connector 24 could be replaced with a wireless communication device of a type known in the art, such as an IR, RF, optical, magnetic, etc. A display panel 28 (e.g., a small LCD or LED screen) is represented as being disposed on the exterior of the housing 18. The circuitry 22 communicates with the display panel 28 to provide the user with information regarding the operation of the sensing unit 12. Power for the sensing element 20, circuitry 22 and panel 28 can be provided with a battery within the housing 18, delivered through a cable connected via the connector 24, or delivered telemetrically using known tele-powering techniques.

The sensing element 20 is represented as comprising a tube 30 that serves as a conduit through which the fluid flows as it flows between an inlet and outlet 32 and 34 of the housing 18. The tube 30 has a U-shaped freestanding portion 36 adapted to be vibrated at resonance in a manner that enables certain properties of the fluid to be measured using Coriolis force principles. A preferred Coriolis-type resonating tube flow sensor is taught in U.S. Pat. No. 6,477,901 to Tadigadapa et al., incorporated herein by reference. In Tadigadapa et al., wafer bonding and silicon etching techniques are used to produce a suspended silicon tube on a wafer, the combination of which is simply referred to as the sensing element 20. The freestanding portion 36 of the tube 30 is vibrated at resonance such that, as fluid flows through the tube 30, the freestanding portion 36 twists under the influence of the Coriolis effect. As explained in Tadigadapa et al., the degree to which the freestanding portion 36 twists (deflects) when vibrated can be correlated to the mass flow rate of the fluid flowing through the tube 30 on the basis of the change in the amplitude of a secondary resonant vibration mode. The density of the fluid is proportional to the natural frequency of the fluid-filled vibrating portion 36, such that controlling the vibration of the portion 36 to maintain a frequency at or near its resonant frequency will result in the vibration frequency changing if the density of the fluid flowing through the tube 30 changes. As depicted in FIG. 1, the freestanding portion 36 is preferably U-shaped, though other shapes—both simpler and more complex—are within the scope of this invention.

The resonating tube flow sensor of Tadigadapa et al. is preferred for use as the sensing unit 12 of this invention, though it is foreseeable that other types of flow sensors could be employed. However, particularly advantageous aspects of the resonating tube sensor of Tadigadapa et al. include its very small size and its ability to precisely measure extremely small amounts of fluids, in contrast to prior art Coriolis-type flow sensors. Furthermore, the preferred flow sensor can attain flow rate measurement accuracies of under +/−1%, in contrast to other types of infusion pumps whose accuracies can range from about +/−15% for volumetric pumps and +/−3% for syringe pumps. While the high cost and the high flow rate requirements for prior art Coriolis-type flow sensors have restricted their use in the drug delivery arena, the flow sensor of Tadigadapa et al. is able to sense the extremely low flow rates (e.g., less than 1 ml/hr) required by infusion therapy applications. Another advantage is that means for vibrating the tube portion and means for sensing movement of the tube portion of the preferred flow sensor uses an electrostatic drive and capacitive sensing (not shown in FIG. 1), which minimizes the power requirements of the sensor. Accordingly, the flow sensor taught by Tadigadapa et al. is ideal for achieving the high accuracy, small size and low power requirements needed for drug infusion systems.

The embodiment of FIG. 1 enables the otherwise conventional syringe 14 to controllably deliver a precise amount of fluid. The mass flow rate and density of the fluid discharged from the syringe 14 by actuating the syringe plunger is detected by the sensing element 20. Mass flow rate, density, and/or the volumetric flow rate computed therefrom by the computer 26 can then be displayed by the display panel 28. Using means for measuring elapsed time during which the fluid has flowed through the housing 18, for example, a timing device associated with the circuitry 22 or computer 26 and triggered when the circuitry 22 measures flow through the tube 30, the volumetric flow rate can be used to calculate and display the actual amount of fluid dispensed through the sensing element 20, thereby giving a very accurate indication of the amount of fluid delivered through the needle 16. Notably, the same precision can be achieved if the fluid source is other than the syringe 14. For example, various manually-operated and machine-operated pumps could be used, such as a pressurized container and other relatively low cost pumps whose lower accuracy would otherwise exclude their use in the medical applications contemplated by the present invention.

Figure 2:
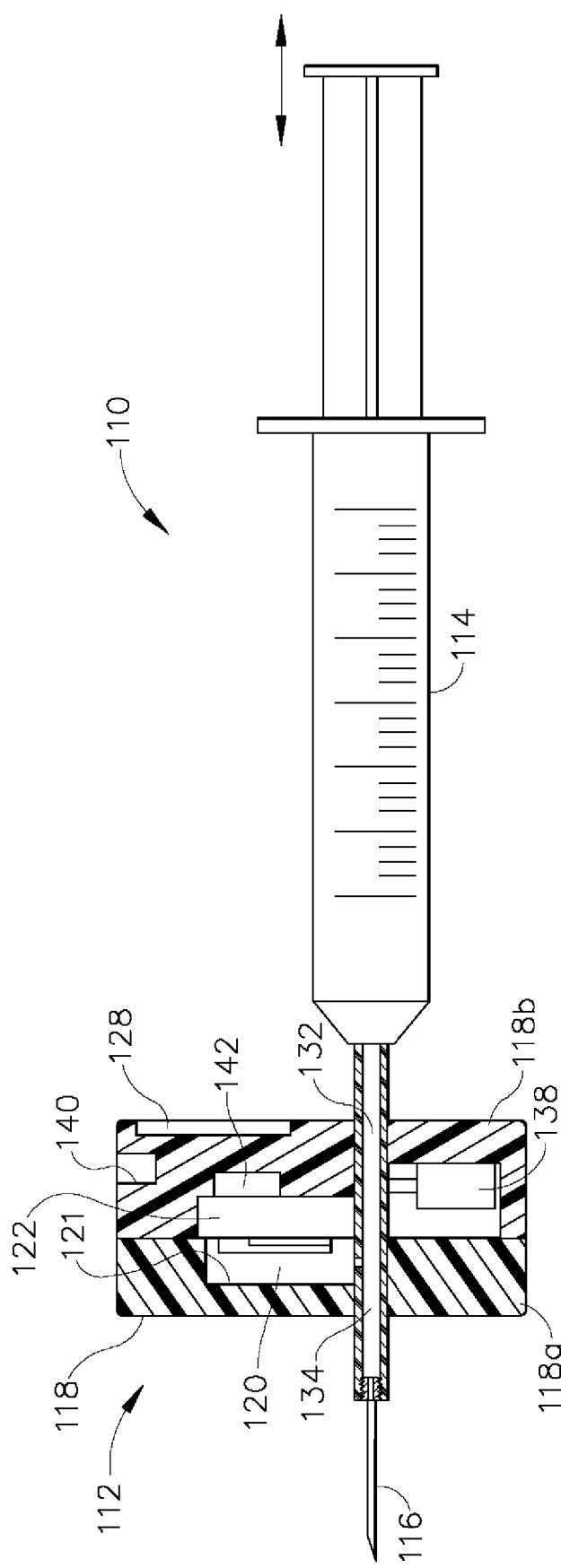
FIG. 2 is a schematic representation of a fluid delivery system similar to the embodiment of FIG. 1, but differing in part by the use of a multi-piece housing in accordance with a second embodiment of the invention.

In the embodiment represented in FIG. 2, a fluid delivery system 110 is shown as being similar to that of FIG. 1, but in which the sensing unit 112 comprises a two-piece housing 118 shown in cross-section. A first portion 118a of the housing 118 defines the housing inlet 132 and outlet 134 and contains the sensing element 120. A second portion 118b of the housing 118 contains components of the unit 112 that do not contact the fluid, e.g., the electronic circuitry 122 and display panel 128, as well as such optional features as a horn 140 or other component for producing an audible or visual signal or alarm, and a battery 142 for powering the unit 112. The housing portion 118b can be configured to plug into the housing member 118a in any suitable manner. Electrical interconnections are preferably made between the housing portions 118a and 118b so that electrical power from the battery 142 in the housing portion 118b is delivered to the sensing element 120 in the housing portion 118a, and output from the sensing element 120 in the housing portion 118a is delivered and processed by the circuitry 122 in the housing portion 118b. Finally, the sensing unit 112 can be equipped with a wireless communication device (not shown) for communication with a computer (not shown), as well as to enable remote programming of the unit 112. Because the components housed within the housing portion 118b do not contact the fluid flowing through the unit 112, the housing portion 118b can be considered a reusable module capable of being installed on any number of similarly-configured housing portions 118a.

As another optional feature, the housing portion 118b is represented as containing an actuator 138 adapted to stop flow of fluid through the housing 118. For example, by forming the inlet 132 to have a pliable membrane or section, the actuator 138 (e.g., in the form of a solenoid) can be operated to pinch or otherwise collapse the pliable section of the inlet 132, thus stopping flow though the housing 118. Alternatively, the actuator 138 could be integrated onto the same micromachined chip as the sensing element 120 to shrink the size and power requirements of the sensing unit 112. Yet another option is to configure the unit 112 to have an actuator capable of pinching an IV tube inserted into the inlet 132 of the housing 118.

Operation of the actuator 138 can be based on a preset condition, such as a specified volume of fluid desired to be dispensed. As discussed above in reference to the embodiment of FIG. 1, the sensing element 120, electronic circuitry 122 and a remote computer (e.g., 26 in FIG. 1) of FIG. 2 can operate to produce outputs that include volumetric flow rate and dosage, the latter of which can be used to signal closure of the actuator 138 (which preferably is normally open to minimize power usage of the sensing unit 112). In such a case, the computer signals the actuator 138 to either restrict or enable flow through the housing 118 based on the output of the circuitry 122.

An important advantage of the fluid delivery system 110 of FIG. 2 is that the housing portion 118b containing those components of the sensing unit 112 that do not contact the fluid, such as the circuitry 120, display panel 128, actuator 138, horn 140, and battery 142, can be configured to be removably mounted to the other housing portion 118a, which can be, if so desired, integrally formed with the syringe 114 as described above in reference to FIG. 1. As such, the housing portion 118a is disposable with the syringe 114, while the reusable housing portion 118b can be installed on a second similarly-configured syringe 114.

Figure 3:
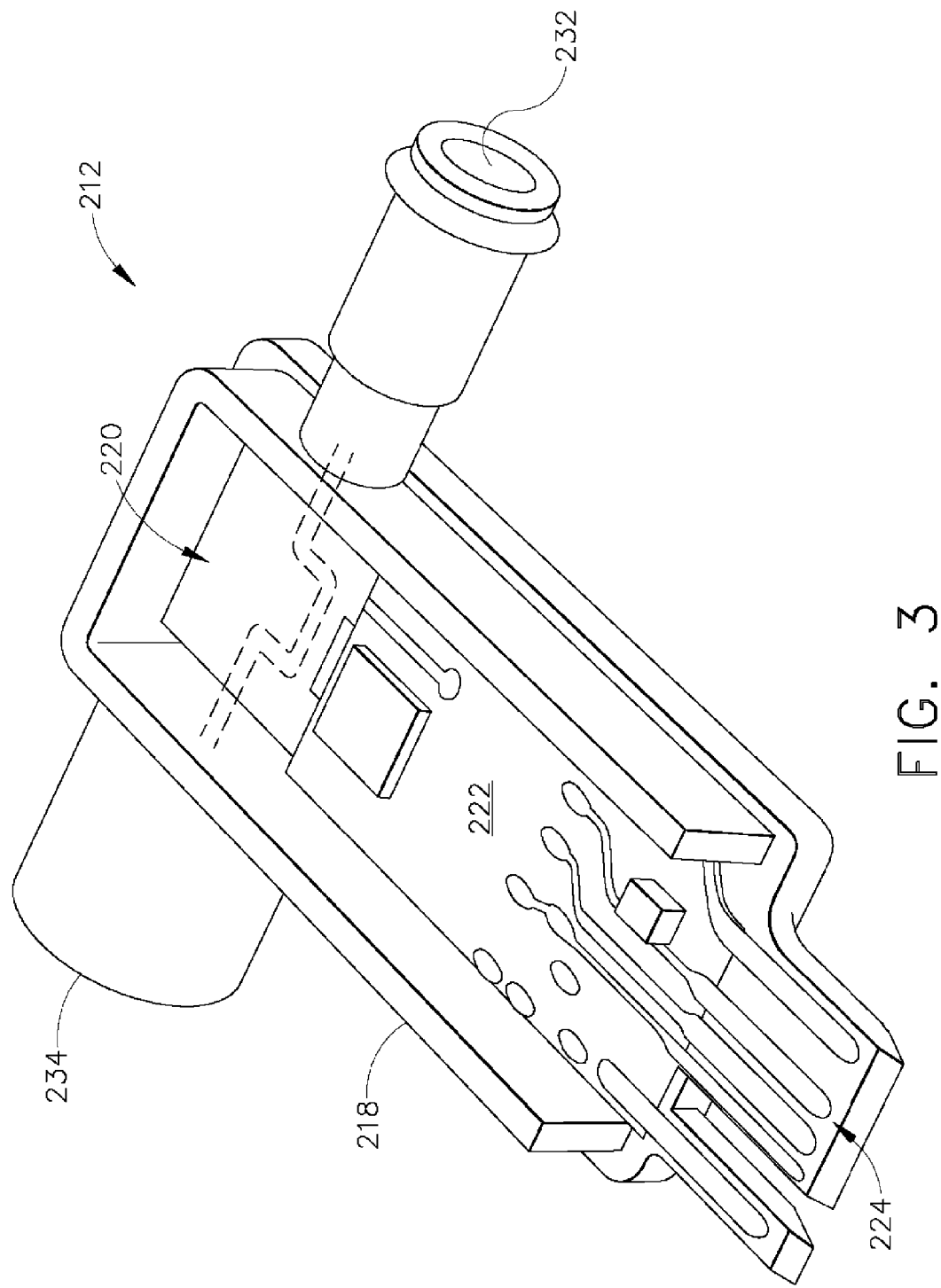
FIG. 3 is a schematic representation of a fluid delivery system suitable for use with a variety of fluid handling equipment in accordance with a third embodiment of the invention.

FIG. 3 represents a sensing unit 212 generally equipped with the same components, including a sensing element 220, circuitry 222, and electrical connector 224, as described for the embodiments of FIGS. 1 and 2, but adapted for being placed inline with, for example, a catheter, Y-tie, septum, IV primer/drip chamber, filter, etc. For example, the inlet 232 on the housing 218 of the sensing unit 212 can be configured to receive a Y-tie equipped with a septum port, while the outlet 234 of the housing 218 is configured to be coupled to a catheter tube. The same benefits as described for the embodiments of FIGS. 1 and 2 can be ascribed to a fluid delivery system the fluid delivery system similarly equipped with the sensing unit 212.

Based on fluid density measurements, the sensing units 12, 112 and 212 are able to detect gas bubbles or another phase within the fluid, and can determine whether, based on density, the correct fluid is being delivered. The safety of an infusion process performed with any of the fluid delivery systems 10, 110 and 210 described above can be promoted with the use of a central computer, such as the computer 26 of FIG. 1. For example, with reference to the delivery system 110 of FIG. 2, a caretaker can program the sensing unit 112 for a specific drug (specific gravity/density range), dose, and dose rate. Should any one or more of these programmed values be exceeded, the sensing unit 112 can give a visual and/or audible warning with the display panel 128 and horn 140, or means disposed within the housing 118, namely, the actuator 138 can be energized to stop drug infusion. Using a central computer and communications provides another layer of patient protection to prevent medication, dose and dose rate errors, all of which cause unwanted death and injury to thousands of patients each year). As an example, in addition to the dose or dose rate being displayed on the display panel 128, a green indicator light (not shown) can be provided that tells the user that the correct drug, dose and dose rate are being sensed; otherwise, a red light or flashing indicator could be used to notify the user that an incorrect drug or dose rate has been detected. Two-way communication between the sensing unit 112 and computer during infusion can be further utilized to alert other caregivers or the infusion system that an error in medicine, dose or dose rate has occurred.

There are a number of drug treatments in which tight flow rate control or dose is critical. Drugs having a narrow therapeutic index (NTI) or range have been defined by the FDA on the basis of the ratio of the median effective dose value of a drug and its median lethal dose or minimum toxic concentration, and whether safe and effective use of the drug requires careful titration and patient monitoring. Such drugs must be administered carefully, as errors in the dose or delivery rate can injure or kill a patient. Additional drugs fall into this category if the patient is an infant or child. Because the sensing units of this invention improve the ability to carefully deliver and monitor the dose of drugs, NTI drugs that are candidates for delivery with this invention include a variety of compounds including, but not restricted to, the following drug or combinations thereof: 5-fluorouracil, acenocumarol, amikacin, aminoglycocides, amniophylline, amphotericin B, anthydisrhythnics, anti-cancer medicines, anticoagulants, anticonvulsants, antifungals, antiretrovirals, carbamazepine, clindamycin, clonidine, coumadin, cyclosporine, depakene, depakote, digitalis glycosides, Digoxin®, Dilantin®, disopyramide, divalproex sodium, dyphilline, eskalith, Gentamicin®, glibenclamide, guanethidine, immunosuppressives, Isoetharine mesylate, isoproterenol, lanoxin, levoxyine, Lidocaine®, lithium, lithium carbonate, Lithobid®, metaporterenol, minoxidil, neural, Norpace®, oxytriphylline, phenobarbital, Phenytoin®, Prazosin®, Primidone®, procainamide, procainbid, pronestyl-sr, quinidine, quinidine gluconate, Quinidix®, quinaglute, Slo-bid®, tacrolimus, Tegretol®, Theo-dur®, theophylline, tobramycin, valproic acid, valproate sodium, vancomycin, Warfarin®, warfarin sodium, and Zidovudine®.

In addition to NTI drugs, other drugs that patients may have an allergic reaction to are excellent candidates for use with the sensing units 12, 112 and 212 of this invention. For this purpose, the flow delivery systems 10, 110 and 210 may serve as means for flowing a fluid through its unit 12, 112 or 212 at a first flow rate and then subsequently at a higher second flow rate, such that the delivery system 10, 110 or 210 can be adapted to gradually administer the drug with very small, gradually increasing doses to begin the desensitization process, permitting the administration of antihistamines if a reaction occurs with the drug. Multiple drugs can be administered in this manner with the sensing units of the invention, including antibiotics and drugs used to treat diseases such as cystic fibrosis, listeria endocarditis and HIV-related PCP.

In view of the above, the sensing units of this invention provide a variety of benefits for a wide array of fluid delivery systems. In addition to the examples given above, the invention provides for an improved syringe pump that conventionally would monitor plunger motion to control drug delivery rates. While low dose syringe pumps can use small syringe barrels to increase their accuracy, the downside is that the total volume that can be pumped accurately with a syringe pump is limited. By inserting a high-accuracy sensing unit of this invention between the syringe and the fluid outlet, a large syringe barrel could be employed while still maintaining high accuracy of small drug volumes because the fluid output is controlled by the sensing unit of this invention instead of the position of the plunger. A stepper motor, often employed in automated syringe pumps, can be used with the invention as an actuator for flow control.

While a timed or preprogrammed dose approach can be taken with the invention, the drug infusion systems described above can also be coupled with other sensors to control the timing and amount of medicines dispensed. For example, a glucose sensor could be used to monitor the glucose level of the blood. When the level goes above or below preset limits, an actuator can be operated to deliver insulin, which is accurately monitored with the sensing unit. Input from the glucose and sensing unit can then used by a computer (e.g., 26 in FIG. 1) to determine when insulin flow should be stopped. Infusion systems of this type could be implanted to treat diabetes, cancer, pain, etc. For additional functionality and safety, a pressure sensor (e.g., a semiconductor pressure sensor on the same chip as the sensing element) can be used to sense occlusions. Furthermore, a filter (not shown) placed upstream of the sensing unit can increase the life of the unit as well as protect the patient.

As evident from the above, sensing units of this invention can be applied to a number of drug infusion accessories, such as: IV bags, Y-ties, cannula, catheters, PICC (Peripherally Inserted Central Catheter), midline catheters, needle tips, AV (Arterial Venus) fistulas, subcutaneous infusion sets, IV tubing sets, filters, Luer fittings, primers, drip chambers, tubing, septums for needle interfacing, scalp vein infusion sets, hemodialysis sets, etc. Furthermore, the sensing units can be employed in fluid delivery using the IV (intravenous), IA (intra arterial), IM (intramuscular), subcutaneous, oral, nasal, trans dermal, and other routes. For drug infusion it is ideal to put the sensing unit as close to the patient as possible, which may require connection to any of the aforementioned accessories. Doing so would enable the sensing unit to monitor any "pushed" or piggybacked drugs, occlusions or air bubbles that are added to the original fluid be administered.

Figure 4:
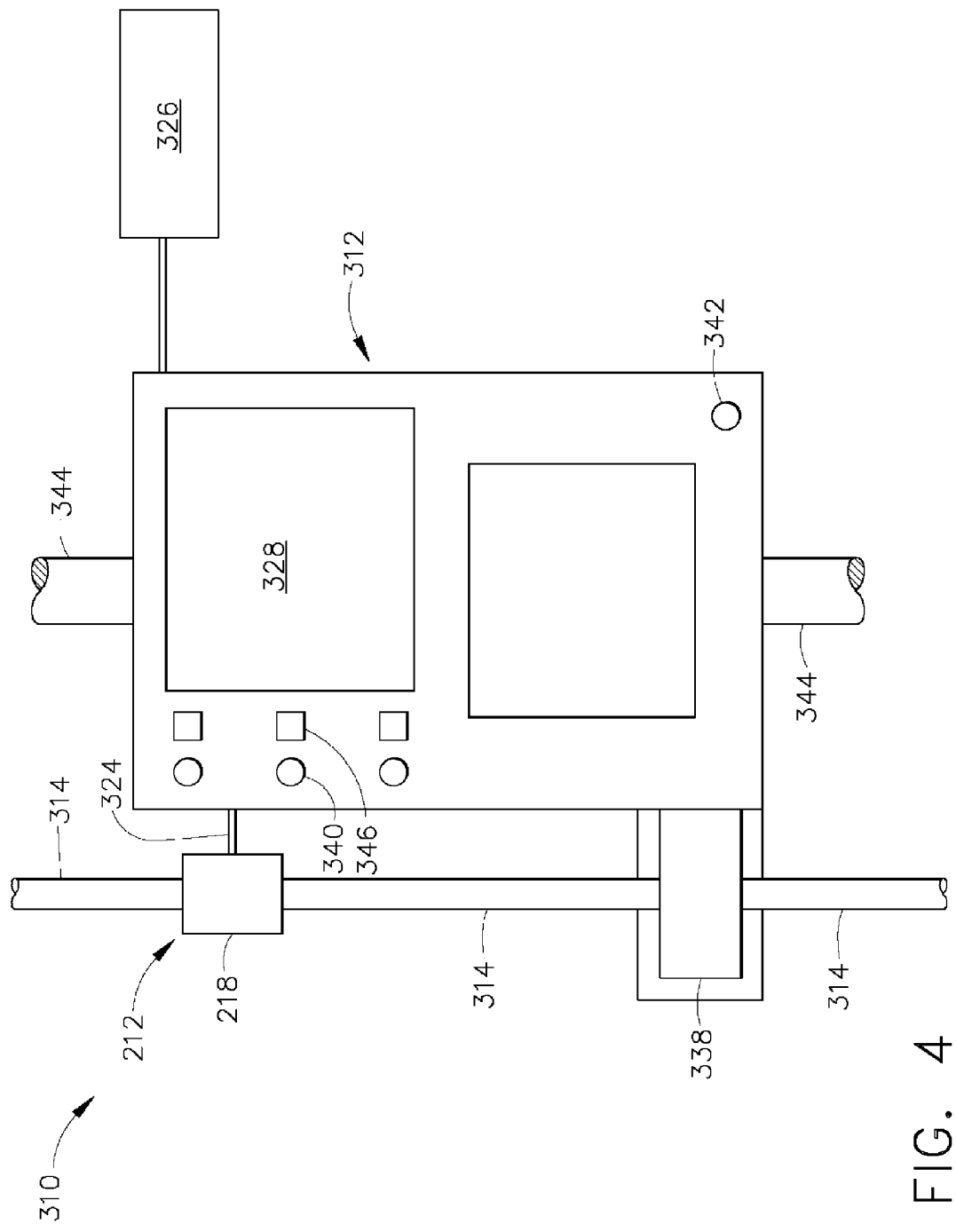
FIG. 4 is a schematic representation of a fluid delivery system mounted to an intravenous pole and adapted to dispense a drug or other medicinal fluid through an intravenous tube in accordance with a fourth embodiment of the invention.

FIG. 4 represents such an infusion system 310 as comprising a module 312 mounted to a standard intravenous pole 344, alongside which an intravenous tube 314 hangs for dispensing a drug or other medicinal fluid. The tube 314 flows into an inline sensing unit that is coupled to the module 312 through an electrical connector 324. The sensing unit can generally be of the type represented in FIG. 3, and is therefore represented with reference number 212. A such, the sensing unit 212 comprises a housing 218, an inlet for receiving the fluid from the tube 314, an outlet for discharging the fluid from the housing 218, at least one cavity between the inlet and outlet, and a sensing element (e.g., 220 in FIG. 3) mounted within the cavity. In view of the discussion above regarding FIG. 3, the sensing unit 212 constitutes means for detecting gas bubbles or another phase within the fluid based on fluid density measurements, and determining whether, based on density, the correct fluid is being delivered. In contrast to the system 210 of FIG. 3, means for providing communication between the sensing unit 212 and module 312, namely, the electronic circuitry (e.g., 222 in FIG. 3) for communicating with the sensing element within the unit 212, is preferably located within the module 312. The module 312 is also equipped with a display 328 for providing a visual indication of the operation of the system 310. An AC power cord (not shown) or rechargeable battery (not shown) may be employed to power both the module 312 and the sensing unit 212. The module 312 is also shown as being equipped with means for displaying a visual output and means for producing an audible output, namely, audible and visual alarms 340, respectively, for warning nearby caregivers of any errors encountered during operation of the system 310, e.g., an improper dose rate, improper density, as well as notifying the caregiver that the intended dose has been delivered, etc. The module 312 can be seen to have other warning indicators and controls, such as a low battery warning light 342 and reset/confirm buttons 346. Finally, means in communication with the module 312 can be provided for stopping flow of the fluid, for example, a shut-off valve 338 is shown as being mounted to the side of the module 312 for stopping flow of the fluid through the intravenous tube 314 in response to the electrical output of the electronic circuitry 222 within the module 312. The module 312 is preferable connected to a computer 326 by which the operation and status of the module 312 can be controlled and monitored. In the embodiment of FIG. 4, the module 312 does not contain any components that contact the fluid, such that and the module 312 constitutes a reusable portion of the infusion system 310 and the sensing unit 212 constitutes a separable disposable portion of the infusion system 310.

While the Coriolis-type flow sensor of Tadigadapa et al. has particular features that make it preferred for use with this application, other types of flow sensors could be used. For example, with certain limitations, hot-wire, thin-film, and drag force flow sensors could be employed in the fluid delivery systems of this invention. Furthermore, while medical applications are of particular interest, non-medical applications also exist for the invention, particularly where precise control of liquids is required. Examples include dispensing and mixing of adhesives, inks, and various chemicals. When used with pipettes and pumps, the sensing units of this invention can be used to extract precise amounts of liquid samples commonly required in biological and chemical analysis, research and development.

While the invention has been described in terms of certain embodiments, it is apparent that other forms could be adopted by one skilled in the art. Therefore, the scope of the invention is to be limited only by the following claims.

The invention claimed is:

1. An infusion system comprising:
an intravenous pole;
an intravenous tube hanging alongside the intravenous pole;
an inline sensing unit coupled to the intravenous tube and comprising a housing, an inlet for receiving a fluid from the intravenous tube, an outlet for discharging the fluid from the housing, at least one cavity between the inlet and the outlet, and a sensing element mounted within the at least one cavity, the sensing element having a first response to the density of the fluid flowing between the inlet and the outlet of the housing, the sensing element having a second response to the mass flow rate of the fluid flowing between the inlet and the outlet of the housing;
a module attached to the intravenous pole, the module comprising electronic circuitry that produces an electrical output based on at least one of the first and second responses of the sensing element, means for displaying a visual output based on the electrical output of the electronic circuitry, means for producing an audible output based on the electrical output of the electronic circuitry;
at least one of means for detecting gas bubbles within the fluid, means for detecting a phase within the fluid, and means for determining the fluid based on the density output of the electronic circuitry; and
means for providing communication between the sensing unit and the module;
wherein the sensing element comprises:
a freestanding tube portion through which the fluid flows;
means for vibrating the freestanding tube portion at a resonant frequency thereof that varies with the density of the fluid flowing therethrough, the resonant frequency of the freestanding tube portion being the first response of the sensing element, the Coriolis effect causing the freestanding tube portion to twist to a degree that varies with the mass flow rate of the fluid flowing therethrough while the freestanding tube portion is vibrated at resonance, the degree of twist being the second response of the sensing element; and
means for sensing movement of the freestanding tube portion to sense the resonant frequency and the degree of twist of the freestanding tube portion as the fluid flows therethrough.

2. The infusion system according to claim 1, wherein the module does not contain components that contact the fluid, the sensing unit constitutes a separable disposable portion of the infusion system, and the module constitutes a reusable portion of the infusion system.

3. The infusion system according to claim 1, further comprising means in communication with the module for stopping flow of the fluid through the intravenous tube in response to the electrical output of the electronic circuitry.

4. The infusion system according to claim 1, further comprising a computer remote from the module and coupled to the module for communication therewith.

* * * * *